United States Patent
Kohl et al.

(10) Patent No.: US 8,541,583 B2
(45) Date of Patent: Sep. 24, 2013

(54) MONOFUNCTIONALIZED PERYLENETETRACARBOXYLIC ACID BISMIDES

(75) Inventors: Christopher Kohl, Mainz (DE); Jianqiang Qu, Mannheim (DE); Klaus Mullen, Cologne (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 190 days.

(21) Appl. No.: 12/852,687

(22) Filed: Aug. 9, 2010

(65) Prior Publication Data

US 2010/0324293 A1    Dec. 23, 2010

Related U.S. Application Data

(62) Division of application No. 10/547,516, filed as application No. PCT/EP2004/001971 on Feb. 27, 2004, now Pat. No. 7,795,432.

(30) Foreign Application Priority Data

Feb. 28, 2003   (DE) .................................. 103 08 941

(51) Int. Cl.
   *C07D 471/08* (2006.01)
   *C07D 471/02* (2006.01)

(52) U.S. Cl.
   USPC ................................................ 546/37; 546/36

(58) Field of Classification Search
   USPC .................................................... 546/37, 36
   See application file for complete search history.

(56) References Cited

FOREIGN PATENT DOCUMENTS

| WO | WO99/31069 A | 6/1999 |
| WO | WO01/69254 A | 9/2001 |

OTHER PUBLICATIONS

Quante et al., "Novel Perylene-Containing Polymers"; Macromolecular Chemistry and Physics, Wiley VCH, Weinheim; vol. 197, Nov. 1996; pp. 4029-4044.

*Primary Examiner* — Charanjit Aulakh
(74) *Attorney, Agent, or Firm* — Sutherland Asbill & Brennan LLP

(57) ABSTRACT

The invention relates to novel perylenetetracarboxylic acid bismide derivatives with improved performance properties.

21 Claims, 1 Drawing Sheet

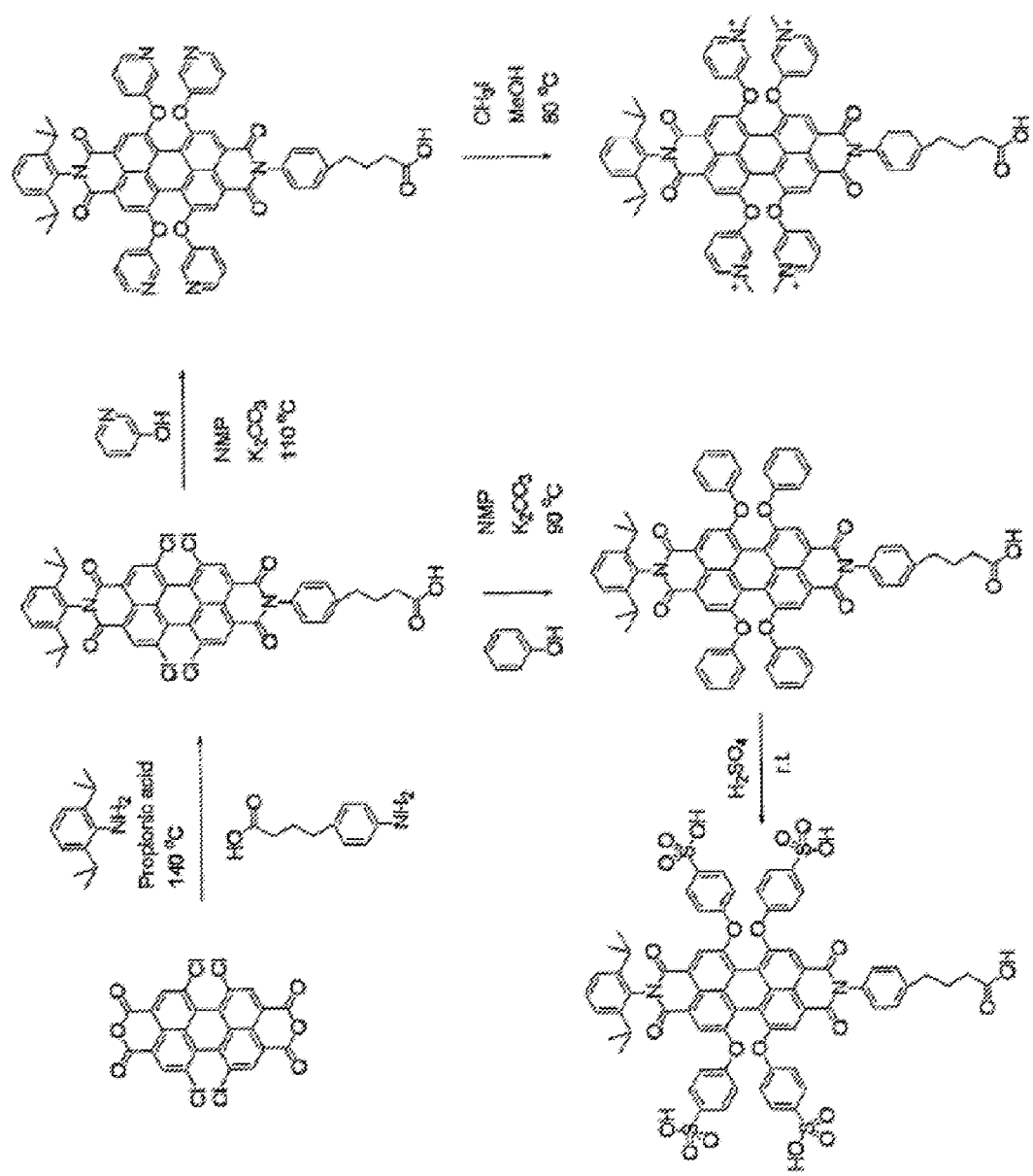

MONOFUNCTIONALIZED PERYLENETETRACARBOXYLIC ACID BISMIDES

CROSS REFERENCES TO RELATED APPLICATIONS

This application is a divisional of U.S. application Ser. No. 10/547,516 filed Aug. 21, 2006 which claims priority to PCT/EP2004/001971 filed on Feb. 27, 2004 and German Application No. 103 08 941.1 filed on Feb. 28, 2003.

DESCRIPTION

The invention relates to novel perylenetetracarboxylic acid bisimide derivatives having improved performance properties.

Perylenetetracarboxylic acid bisimides are known for their exceptional thermal, chemical and photophysical stability (1). They are used as dyes and pigments, for example in reprographic processes (2), fluorescent solar collectors (3), photovoltaic cells (4) and dye lasers (5). A further possible field of application is the use as labeling groups in detection processes, in particular in diagnostic or analytical processes on biological samples, including living cells. Many of these applications are based on the high fluorescence intensity of the perylene chromophore group and on the fact that the fluorescence excitation emission wavelengths of perylenetetracarboxylic acid bisimides lie at wavelengths of above 500 nm, at which signal disruptions caused by autofluorescence of cells, biological tissues or biological liquids are negligible.

However, one disadvantage of known perylenetetracarboxylic acid bisimides is that they have poor water solubility and/or weak fluorescence intensity in water (6). These disadvantages are brought about mainly by the aggregation of dye molecules in a hydrophilic environment, as a result of which the number of biological applications is limited (7).

DE-A-37 03 513 describes perylenetetracarboxylic acid bisimides which have one or more sulfonic acid radicals in the imide structure.

Quante et al. (Macromol. Chem. Phys. 197 (1996), 4029-4044) disclose perylenetetracarboxylic acid bisimides which contain sulfonic acid groups on the basic skeleton of the perylene chromophore. Further modified perylenetetracarboxylic acid bisimides are described in EP-A-0 648 817, EP-A-0 654 504, U.S. Pat. No. 4,378,302, EP-A-0 869 959, WO 97/22607 and by Zhubanov et al. (Zh. Org. Khim. 28 (1992), 1486-1488).

EP 0 896 964 discloses perylene hydrazide imides which can be used as a detection reagent for carbonyl compounds.

WO 02/14414 discloses functionalized perylenetetracarboxylic acid bisimides which are provided as initiators or/and as reaction partners for polymerization reactions.

These compounds exhibit increased fluorescence in aqueous solutions. However, it has not been possible to fully eliminate the disadvantages of the prior art, in particular the tendency to aggregate formation in aqueous solutions.

There is therefore a great need to provide novel perylenetetracarboxylic acid bisimides having improved properties, in particular with regard to the ability to couple to binding partners, to the water solubility or/and to the fluorescence intensity in water or aqueous media.

This object is achieved in accordance with the invention by providing monofunctionalized perylenetetracarboxylic acid bisimides which preferably have at least two hydrophilic groups on the basic skeleton of the perylene chromophore. These exhibit fluorescence quantum yields of up to 80% in water and can be coupled in a defined manner to binding partners, for example biomolecules.

The invention thus provides perylenetetracarboxylic acid bisimides of the structural formula (I)

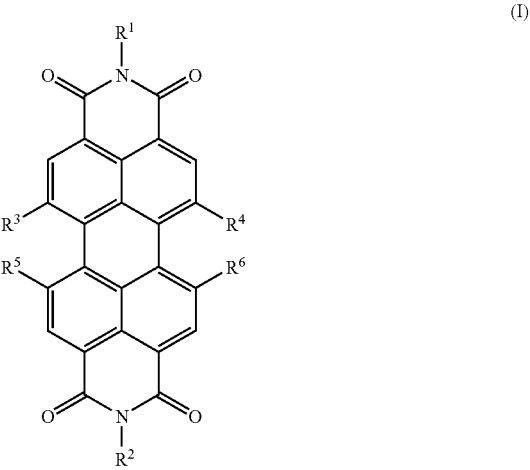

(I)

in which $R^1$ and $R^2$ are different organic radicals, one of the radicals having a group for coupling to a binding partner, and at least two of $R^3$, $R^4$, $R^5$ and $R^6$ are each independently organic radicals which contain at least one hydrophilic group.

An essential feature of the invention is that the compounds (I) are monofunctionalized compounds, i.e. compounds in which one of the two radicals $R^1$ and $R^2$ has a group for coupling to a binding partner. These coupling groups are preferably reactive functionalities which enable coupling to binding partners, in particular to amino, thiol or/and carboxyl groups in biological substances, or precursors of such reactive functionalities. Examples of suitable biological substances are nucleobases, nucleosides, nucleotides and analogs thereof, for example nucleotide derivatives for the chemical synthesis of nucleic acids, such as phosphoramidites, nucleic acids such as DNA or RNA, or else nucleic acid analogs, for instance PNA or LNA, amino acids, amino acid derivatives, peptides, polypeptides, glycoproteins, mono-, oligo- and polysaccharides, lipids, etc.

Examples of suitable reactive functionalities are active esters, maleimides, isocyanates, sulfonyl halides, carbonyl halides, in particular carbonyl chlorides, iodoacetamides, aziridines, epoxides, acyl azides and acyl nitriles. Examples of precursors of reactive functionalities are sulfonic acid groups and carboxylic acid groups which can be converted to reactive functionalities by known methods. This conversion is effected preferably after the synthesis of the basic skeleton of the compound, and it is possible if appropriate to additionally use protecting groups to prevent undesired side reactions, for example at the $R^3$, $R^4$, $R^5$ and $R^6$ positions.

The $R^1$ and $R^2$ radicals present as part of the imide structure are preferably bonded via a secondary or tertiary carbon atom to the imide nitrogen atom, although a bond via a primary carbon atom, i.e. via a $CH_2$ group, is also possible. $R^1$ and $R^2$ are more preferably secondary or tertiary aliphatic radicals or cyclic radicals having typically 3-30 carbon atoms, in particular mono- or bicyclic, aromatic or heteroaromatic radicals, for instance phenyl, pyridyl or naphthyl, which optionally bear one or more substituents. Examples of suitable substituents for aliphatic or saturated cyclic radicals are CN, $NO_2$, halogen (e.g. F, Cl, Br or I), OH, $OR^7$, $OCOR^7$, SH, $SR^7$, $SCOR^7$, $SO_2R^7$, CHO, $COR^7$, COOH, COOM, $COOR^7$, $CONH_2$, $CONHR^7$, $CON(R^7)_2$, $SO_3H$, $SO_3M$, $SO_3R^7$, $NH_2$, $NHR^7$ or $N(R^7)_2$, where M is a cation, e.g. an alkali metal ion such as sodium, potassium, etc., and $R^7$ is an optionally halogen-substituted $C_1$-$C_6$-alkyl radical. Cyclic radicals, for example aromatic or heteroaromatic radicals, may additionally be substituted by one or more $R^7$ radicals.

At least two of the $R^3$, $R^4$, $R^5$ and $R^6$ radicals bear at least one hydrophilic group. Preferably all four $R^3$, $R^4$, $R^5$ and $R^6$ radicals bear at least one hydrophilic group. The hydrophilic group may be an uncharged or charged group. Examples of suitable uncharged groups are hydroxyl groups and polyoxy-$C_2$-$C_4$-alkylene groups, in particular polyoxyethylene groups, having three or more, for example up to 50 or 100, alkylene oxide units. However, the hydrophilic group is preferably a charged group, i.e. a group which is charged in neutral media, for example at pH 7, for example a positively charged group, for instance an amino group or an ammonium group, in particular a quaternized ammonium group, or an alkylated heteroaromatic nitrogen atom, in particular an N-alkylpyridinium, N-alkylquinolinium or N-alkylisoquinolinium group, where the alkyl radical preferably has up to 6 carbon atoms and may optionally be substituted as described above. Examples of suitable negatively charged groups are sulfonic acid or carboxylic acid groups, $SO_3H$ and COOH, and also their $SO_3M$ and COOM salts, where M is a cation, for example an alkali metal ion, for instance potassium or sodium. In addition, $R^3$, $R^4$, $R^5$ or/and $R^6$ may also contain a plurality of identically or oppositely charged groups, amphiphilic groups being formed in the latter case. Particularly preferred amphiphilic groups are heteroaromatic nitrogen atoms which are alkylated by a radical which bears a —$CO_2H$, —$SO_3H$, —$CO_2M$ or —$SO_3M$ group.

It is also preferred that at least two of the $R^3$, $R^4$, $R^5$ and $R^6$ radicals include aromatic or heteroaromatic radicals, in particular monocyclic or bicyclic radicals, for instance phenyl or pyridine.

In a particularly preferred embodiment, at least two of $R^3$, $R^4$, $R^5$ and $R^6$ are represented by the general structural formula (II)

  (II)

in which Ar is an aromatic or heteroaromatic radical which contains at least one hydrophilic group, for example a charged group as specified above. In the case that perylenetetracarboxylic acid bisimides having negative charge carriers are used, at least one of $R^3$, $R^4$, $R^5$ and $R^6$ may have the general structural formula (III):

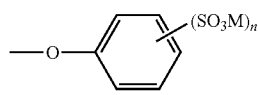  (III)

in which M is a cation and n is 1, 2 or 3.

In the case of the use of perylenetetracarboxylic acid bisimides having positive charge carriers, at least one of $R^3$, $R^4$, $R^5$ and $R^6$ may have the general structural formula (IV):

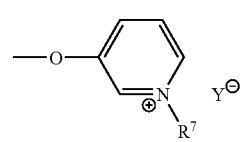  (IV)

in which $R^7$ is an optionally substituted $C_1$-$C_6$-alkyl radical, preferably $C_1$-$C_4$-alkyl radical, and Y is an anion, e.g. a halide ion. When the $R^7$ radical bears a negatively charged group as a substituent, an amphiphilic radical is obtained.

The inventive perylenetetracarboxylic acid bisimides are typically prepared from an industrially readily obtainable di- or tetra-halo-substituted perylenetetracarboxylic bis-anhydride of the general structural formula (V)

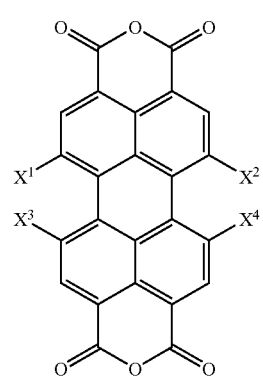  (V)

in which at least two of $X^1$, $X^2$, $X^3$ and $X^4$ are halogen, in particular Cl or Br, and the others are hydrogen, by condensation with two different primary amines, $H_2NR^1$ and $H_2NR^2$, in which $R^1$ and $R^2$ are each as defined above. Particularly preferred molar ratios of the amines are from 1 to 3 equivalents of amine based on 1 equivalent of di- or tetra-halo-substituted perylenetetra-carboxylic bisanhydride, the sterically more demanding amine being used in a higher excess. Surprisingly, it has been found that a mixed substituted product is obtained in high yield in this reaction and can be removed directly from any by-products which occur, for example by column chromatography. The resulting halogen-substituted perylenetetracarboxylic acid bisimides of the general structural formula (VI)

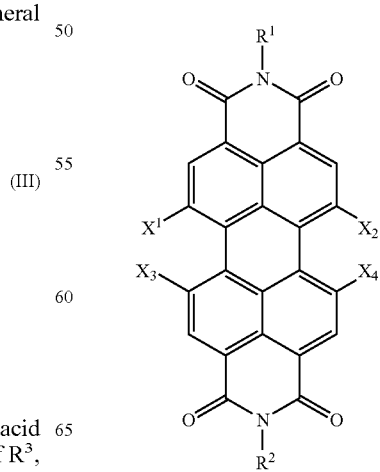  (VI)

in which at least two of $X^1$, $X^2$, $X^3$ and $X^4$ are halogen, in particular Cl or Br, and the others are hydrogen are subsequently reacted with a compound of the general structural formula (VII)

$$HO-Ar' \qquad (VII)$$

in which Ar' is an aromatic or heteroaromatic radical. This reaction forms tetra-substituted perylenetetracarboxylic acid bisimides of the general structural formula (VIIIa) or disubstituted perylene-tetracarboxylic acid bisimides of the general structural formula (VIIIb):

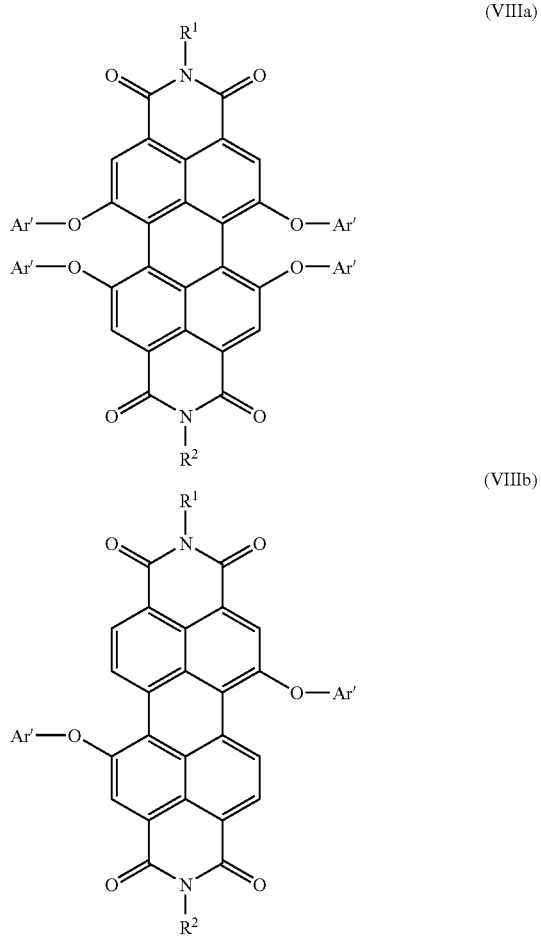

Subsequently, hydrophilic groups, as specified above, may be introduced into the aromatic or heteroaromatic Ar' radicals. For example, at least one $SO_3H$ or $SO_3M$ group may be introduced into Ar' by reaction with $H_2SO_4$ under suitable conditions. Alternatively, heteroaromatic nitrogen atoms in Ar' may be alkylated, for example by reacting with an alkyl halide, e.g. $CH_3I$, under suitable conditions.

After synthesis of the basic skeleton of the compound, the precursor of a reactive functionality in $R^1$ or $R^2$ may be converted to the reactive functionality itself.

The monofunctionalized compounds (I) may subsequently, if appropriate after removal of protecting groups, be coupled covalently to a binding partner, for example a biomolecule as specified above. The invention thus also relates to conjugates of the compounds (I) with a binding partner.

The inventive compounds may also be employed in all technical fields suitable for the use of perylenetetracarboxylic acid bisimides, for example in dye lasers, as labeling groups in analytical processes, as tracers, in scintillation counters, in fluorescence solar collectors, in liquid crystals, in cold light sources, in materials testing, as photoconductors, in photographic processes, in illumination and display elements, as semiconductors, etc.

The compounds or their conjugates, for example covalent conjugates with biomolecules such as nucleic acids, proteins, peptides, saccharides, etc., may be dissolved in liquids, for example organic or/and aqueous solvents, or in solids, for example plastics.

BRIEF DESCRIPTION OF THE DRAWINGS

The present invention will be further illustrated by figures and examples.

FIG. 1 shows a reaction scheme for the preparation of the tetra-substituted compounds specified in examples 1-5.

EXAMPLES

Example 1

Preparation of N-(2,6-diisopropylphenyl)-N'-[(4-butyric acid)phenyl]-1,6,7,12-tetrachloro-perylene-3,4:9,10-tetracarboxylic acid bisimide A mixture of 13.25 g (25 mmol) of tetrachloroperylene-3,4:9,10-tetracarboxylic bisanhydride, 13.5 g of diisopropylaniline and 5 g (28 mmol) of butyroaniline in 400 ml of propionic acid were heated to 140° C. under argon in a Schlenk flask and left at this temperature for 12 h. After cooling to room temperature, the reaction mixture was poured into water and the crude product was collected by filtration. The desired differently N,N'-substituted product was purified by column chromatography on silica gel using $CH_2Cl_2$/acetone (20:1) as the eluent.

M.P.: >300° C.; 1H NMR (250 MHz, $CD_2Cl_2$, 300 κ): δ[ppm]: 8.76 (s, 2H), 8.74 (s, 2H), 7.54 (t, 1H), 7.45 (d, 2H), 7.38 (d, 2H), 7.28 (d, 2H), 2.80 (m, 4H), 2.73 (m, 2H); 2.09 (m, 2H), 1.16 (d, 12H). UV-Vis spectrum (chloroform) $\lambda_{max}$ (ε)=527 (46791), 494 (32499), 436 nm (12120 $M^{-1}$ $cm^{-1}$), Fluorescence spectrum (chloroform) $\lambda_{max}$=553 nm. FD mass spectrum (8 kV):m/z=849.7 (100%) [$M^+$] (Cal. 850.5)

Example 2

Preparation of N-(2,6-diisopropylphenyl)-N'-[(4-butyric acid)phenyl]-1,6,7,12-tetraphenoxy-perylene-3,4:9,10-tetracarboxylic acid bisimide 8.48 g (10 mmol) of the compound prepared in example 1, 5.4 g (100 mmol) of phenol and 8.62 g (68.5 mmol) of $K_2CO_3$ were suspended under an inert gas atmosphere in 400 mmol of N-methylpyrrolidone (NMP). The reaction mixture was heated to 90° C. and stirred for 24 h. After cooling to room temperature, the mixture was poured into 5 l of aqueous HCl. The resulting precipitate was filtered, washed to neutrality and dried at 75° C. under reduced pressure. The product was further purified by chromatography on silica gel with $CH_2Cl_2$/acetone (10:1) as the eluent.

M.P.: >300° C.; $^1$H NMR (250 MHz, $CD_2Cl_2$,300 κ): δ[ppm]:8.18 (s, 2H), 8.17 (s, 2H), 7.46 (t, 1H), 7.31 (m, 12H), 7.15 (m, 6H), 7.00 (d, 8H); 2.72 (m, 4H), 2.42 (m, 2H), 2.01 (m, 2H), 1.09 (d, 12H). UV-Vis spectrum (chloroform)

$\lambda_{max}$=573, 546 nm; fluorescence spectrum (chloroform) $\lambda_{max}$, =605 nm. FD mass spectrum (8 kV):m/z=1081.8 (100%) [M$^+$](Cal. 1081.1)

Example 3

Preparation of N-(2,6-diisopropylphenyl)-N'-[(4-butyric acid)phenyl]-1,6,7,12-tetra(4-sulfonyl-phenoxy)perylene-3, 4:9,10-tetracarboxylic acid bisimide 0.5 g (0.46 mmol) of the compound prepared in example 2 was dissolved in 1 ml of concentrated sulfuric acid and stirred at room temperature (20° C.) for 16 h. The product was precipitated by addition of water, filtered and dried at 75° C. under reduced pressure.

M.P.: >300° C.; $^1$H NMR (250 MHz, MeOD, 300 κ): δ[ppm]: 8.01 (s, 2H), 7.99 (s, 2H), 7.69 (d, 4H), 7.65 (d, 2H), 7.25 (t, 1H), 7.12 (m, 6H), 6.95 (m, 8H), 2.56 (m, 4H), 2.20 (m, 2H); 1.82 (m, 2H), 0.94 (d, 12H). UV-Vis spectrum (water) $\lambda_{max}$=575, 546 nm; fluorescence spectrum (water) $\lambda_{max}$=607 nm; MALDI-TOF mass spectrum m/z=1402.1 (100%) [M$^+$](Cal. 1401.4).

Example 4

Preparation of N-(2,6-diisopropylphenyl)-N'-[(4-butyric acid)phenyl]-1,6,7,12-tetra(3-pyridoxy)perylene-3, 4:9,10-tetracarboxylic acid bisimide 1.5 g (1.77 mmol) of the compound prepared in example 1, 1,1 g (10.7 mmol) of 3-hydroxypyridine and 1.2 g (0.8 mmol) of K$_2$CO$_3$ were dissolved in 150 ml of NMP. The reaction mixture was stirred at 110° C. under an inert gas atmosphere. After 36 h, the mixture was cooled to room temperature and neutralized with dilute hydrochloric acid. The crude product was filtered, washed with water and dried at 75° C. under reduced pressure. The resulting solid was further purified by chromatography on silica gel using CH$_2$Cl$_2$/acetone (10:1) as the eluent.

M.P.: >300° C.; $^1$H-NMR (250 MHz, CD$_2$Cl$_2$, 300 κ): δ[ppm]: 8.33 (m, 8H), 8.23 (s, 2H), 8.19 (s, 2H), 7.46 (t, 1H), 7.36-7.15 (m, 14H), 2.71 (m, 4H), 2.38 (m, 2H), 1.98 (m, 2H), 1.08 (d, 12H). UV-Vis spectrum (chloroform) $\lambda_{max}$(ε)=564 (50150), 528 (32536), 446 nm (16523 M$^{-1}$ cm$^{-1}$); fluorescence spectrum (chloroform) $\lambda_{max}$=595 nm. FD mass spectrum (8 kV):m/z=1086.2 (100%) [M$^+$] (Cal. 1085.1).

Example 5

Preparation of N-(2,6-diisopropylphenyl)-N'-[(4-butyric acid)phenyl]-1,6,7,12-tetra[(N-methylpyridinium)oxy]perylene-3, 4:9,10-tetracarboxylic acid bisimide 300 mg (0.28 mmol) of the compound prepared in example 4 were dissolved at 80° C. in 100 ml of methanol. 2 ml of methyl iodide were added to the stirred solution and the mixture was kept under reflux for 48 h. The resulting product was obtained in high purity.

M.P.: >300° C.; 1H NMR (250 MHz, MeOD, 300 κ): δ[ppm]: 9.52-9.29 (m, 4H), 9.06 (m, 4H), 8.83-8.77 (m, 8H), 8.38 (m, 4H), 7.80 (t, 1H), 7.70 (m, 4H), 7.60 (d, 2H), 5.27 (s, 12H), 3.10 (m, 4H), 2.75 (m, 2H), 2.36 (m, 2H), 1.45 (d, 12H). UV-Vis spectrum (water) $\lambda_{max}$(ε)=547 (29974), 525 (23496), 432 nm (9456 M$^{-1}$ cm$^{-1}$); fluorescence spectrum (water) $\lambda_{max}$=591 nm.

Example 6

Preparation of Disubstituted Perylenetetracarboxylic Acid Bisimides

Starting from N,N'-bis(2,6-diisopropylphenyl)-1,7-dibromoperylene-3,4:9,10-tetracarboxylic acid bisimide, N-(2,6-diisopropylphenyl)-N'-[(4-butyric acid)phenyl]-1,7-di(4-sulfonylphenoxy)perylene-3,4:9,10-tetracarboxylic acid bisimide was prepared according to the reaction sequence described in examples 1 to 3, and N-(2,6-diisopropylphenyl)-N'-[(4-butyric acid)phenyl]-1,7-di[3-(N-methylpyridinium)oxy]perylene-3, 4:9,10-tetracarboxylic acid bisimide was prepared according to the reaction sequence described in examples 1 and 4-5.

REFERENCES (1) Y. Nagao and T. Misono, Dyes Pigm., 1984, 5, 171
A. Rademacher, S. Merkle and H. Lanhals, Chem. Ber. 1982, 115, 2927

(2) H. O. Loutfy, A. M. Hor, P. Kazmaier and M. Tam, J. Imaging Sci., 1989, 33, 151

(3) G. Seybold and G. Wagenblast, Dyes Pigm. 1989, 11, 303

(4) L. Schmidt-Mende, A. Fechtenkötter, K. Müllen, E. Moons, R. H. Friend, J. D. MacKenzie, Science, 2001, 293, 1119

(5) R. Gvishi, R. Reisfeld and Z. Burshteim, Chem. Phys. Lett., 1993, 213, 338

(6) H. Icil, D. Uzun and N. Pasaogullari, Spectrosc. Lett., 1998, 31, 667 S. Icil. S. Demic, B. Dindar, A. O. Doroshenko and C. Timur, J. Photochem. Photobiol., 2000, 136, 15
H. Quante, P. Schlichting, U. Rohr, Y. Geerts and K. Müllen, Macromol. Chem. Phys., 1996, 197, 4029
W. Bauer, D. Baumgart, D. Schnaltmann, K.-P. Kreutzer and W. Zöller, EP 0 832 937 B1
H.-A. Klok, J. Rodriguez Hernandez, S. Becker and K. Müllen, J. Polym. Sci., 2001, 39, 1572

(7) H. Han, R. J. Bennett and L. H. Hurley, Biochem. 2000, 39, 9311
N. V. Khromov-Borisov, M. L. Indenbom and A. F. Danilov, Pharm. Chem. J. 1980, 14, 90

The invention claimed is:

1. A perylenetetracarboxylic acid bisimide of the structural formula (I)

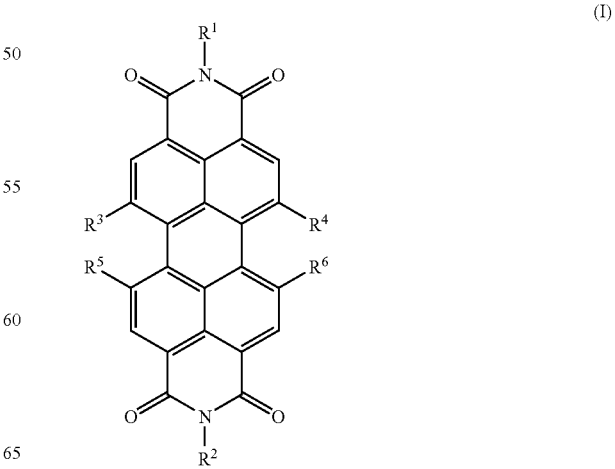

and wherein R3, R4, R5 or/and R6 comprise aromatic or heteroaromatic radicals, wherein $R^1$ and $R^2$ are different organic radicals selected independently from secondary or tertiary aliphatic radicals or, substituted or unsubstituted, mono- or bicyclic, aromatic, or heteroaromatic radicals having 3-30 carbon atoms, one of the radicals having a group for coupling to a binding partner selected from the group consisting of active esters, maleimides, isocyanates, sulfonyl halides, carbonyl halides, iodoacetamides, aziridines, epoxides, acyl azides, acyl nitriles, sulfonic acid groups, and carboxylic acid groups, and at least two of $R^3$, $R^4$, $R^5$ and $R^6$ are each independently aromatic or heteroaromatic radicals which contain at least one uncharged, positively charged, or negatively charged hydrophilic group, and the uncharged hydrophilic groups are selected from hydroxyl groups or polyoxy -$C_2$-$C_4$-alkylene groups, the positively charged hydrophilic groups are selected from amino groups or ammonium groups, and the negatively charged hydrophilic groups are selected from $SO_3H$, COOH, $SO_3M$, or COOM, wherein M is a cation, and at least one of $R^3$, $R^4$, $R^5$ and $R^6$ has the general structural formula (III):

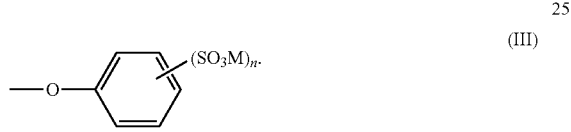

wherein n is an integer of 1-3.

2. A compound as claimed in claim 1,
wherein
the coupling group is a reactive functionality for binding to amino, thiol or carboxyl groups or a precursor thereof.

3. A compound as claimed in claim 1,
wherein
the coupling group is an active ester, maleimide, isocyanate, sulfonyl halide, carbonyl halide, iodoacetamide, aziridine, epoxide, acvl azide, acvl nitrile or a precursor thereof.

4. A compound as claimed in claim 1,
wherein
$R^1$ or/and $R^2$ are aromatic or heteroaromatic radicals, which optionally contain one or more substituents.

5. A compound as claimed in claim 1,
wherein
at least two of $R^3$, $R^4$, $R^5$ and $R^6$ are an organic radical which bears an uncharged hydrophilic group.

6. A compound as claimed in claim 1,
wherein
at least two of $R^3$, $R^4$, $R^5$ and $R^6$ are each independently an organic radical which bears a positively charged (in neutral media) group.

7. A compound as claimed in claim 1,
wherein
at least two of $R^3$, $R^4$, $R^5$ and $R^6$ are each independently an organic radical which bears a group selected from quaternary ammonium and N-alkylated heteroaromatic N groups such as N-alkylpyridinium, N-alkylquinolinium or N-alkylisoquinolinium groups.

8. A compound as claimed in claim 1,
wherein
$R^3$, $R^4$, $R^5$ and $R^6$ are each independently an organic radical which bears a negatively charged (in neutral media) group.

9. A compound as claimed in claim 1,
wherein
at least two of $R^3$, $R^4$, $R^5$ and $R^6$ are each independently an organic radical which bears a group selected from $SO_3H$, COOH, $SO_3M$ and COOM, wherein M is a cation.

10. A compound as claimed in claim 1,
wherein
at least three of $R^3$, $R^4$, $R^5$ or/and $R^6$ are an organic radical which carries a charged group.

11. A compound as claimed in claim 1,
wherein
all four of $R^3$, $R^4$, $R^5$ and $R^6$ are an organic radical which carries a charged group.

12. A compound, as claimed in claim 1,
wherein
at least one of $R^3$, $R^4$, $R^5$ and $R^6$ has the general structural formula (II):

wherein Ar is an aromatic or heteroaromatic radical which contains at least one charged group.

13. A conjugate of compounds as claimed in claim 1 with a binding partner.

14. The conjugate as claimed in claim 13,
wherein
the binding partner is a biomolecule.

15. A process for preparing perylenetetracarboxylic acid bisimides of the general structural formula (I), of claim 1 comprising the steps of:

(a) reacting halogen-substituted perylenedi- or perylenetetracarboxylic anhydrides of the general structural formula (V):

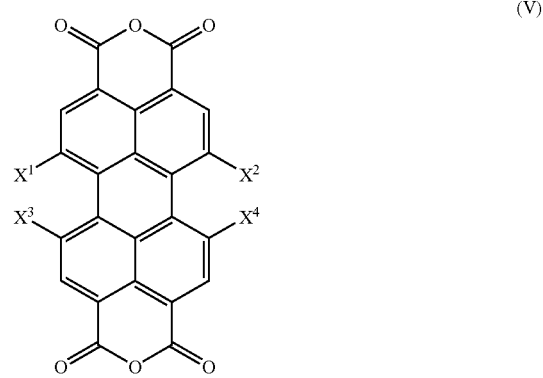

wherein at least two of $X^1$, $X^2$, $X^3$ and $X^4$ are halogen and the others are hydrogen with a mixture of two different amines $H_2NR^1$ and $H_2NR^2$, wherein $R^1$ and $R^2$ are each as defined in claim 1, to give a compound of the general structural formula (VI)

(VI)

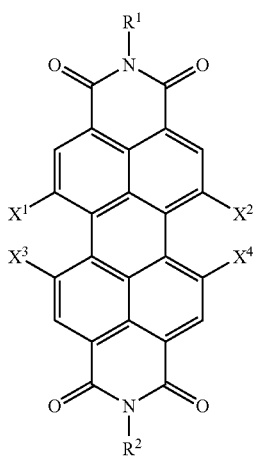

(b) reacting the compound (VI) with a compound of the general structural formula (VII):

HO—Ar' (VII)

wherein Ar' is an aromatic or heteroaromatic radical to give tetra-substituted perylenetetracarboxylic acid bisimides of the general structural formula (VIIIa) or to give disubstituted perylenetetracarboxylic acid bisimides of the general structural formula (VIIIb):

(VIIIa)

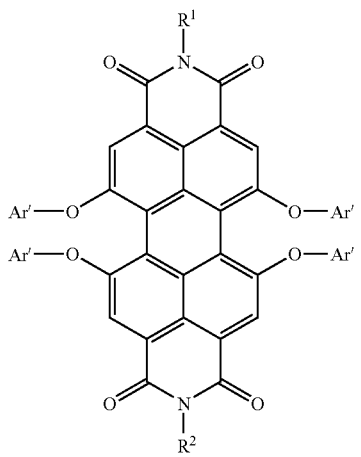

(VIIIb)

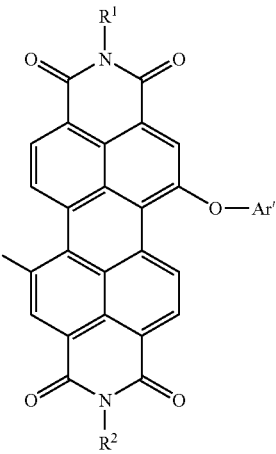

and (c) introducing hydrophilic groups into the aromatic or heteroaromatic Ar' radicals.

16. The process as claimed in claim 15, wherein step (b) includes the introduction of at least one $SO_3H$ or $SO_3M$ group into Ar', where M is a cation.

17. The process as claimed in claim 15, wherein step (b) includes the alkylation of at least one heteroaromatic N atom in Ar'.

18. A compound as claimed in claim 1, wherein $R^1$ and $R^2$ are independently selected from the mono- or bicyclic, aromatic or heteroaromatic radicals that are substituted or unsubstituted.

19. A compound as claimed in claim 18, wherein mono- or bicyclic, aromatic or heteroaromatic radicals are independently selected from, unsubstituted or substituted, phenyl, pyridyl, or naphthyl radicals.

20. A compound as claimed in claim 1, wherein the aromatic or heteroaromatic radicals are selected from phenyl or pyridyl radicals.

21. A compound as claimed in claim 4, wherein the aromatic or heteroaromatic radicals are selected from phenyl, pyridyl, or naphthyl radicals.

* * * * *

UNITED STATES PATENT AND TRADEMARK OFFICE
CERTIFICATE OF CORRECTION

| | |
|---|---|
| PATENT NO. | : 8,541,583 B2 |
| APPLICATION NO. | : 12/852687 |
| DATED | : September 24, 2013 |
| INVENTOR(S) | : Christopher Kohl et al. |

It is certified that error appears in the above-identified patent and that said Letters Patent is hereby corrected as shown below:

In the Claims

At column 9, line 43, delete "acvl" and insert -- acyl --.

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO.      : 8,541,583 B2  
APPLICATION NO. : 12/852687  
DATED           : September 24, 2013  
INVENTOR(S)     : Christopher Kohl et al.

Page 1 of 1

It is certified that error appears in the above-identified patent and that said Letters Patent is hereby corrected as shown below:

In the Claims

At column 9, lines 1-2, delete "and wherein R3, R4, R5 or/and R6 comprise aromatic or heteroaromatic radicals,".

At column 9, line 15, after "hydrophilic group," insert -- and wherein R3, R4, R5 or/and R6 comprise aromatic or heteroaromatic radicals, --

Signed and Sealed this  
Thirteenth Day of May, 2014

Michelle K. Lee  
*Deputy Director of the United States Patent and Trademark Office*